United States Patent
Bert et al.

(10) Patent No.: US 9,119,962 B2
(45) Date of Patent: Sep. 1, 2015

(54) METHOD AND DEVICE FOR CONTROLLING DOSAGE APPLICATION DURING IRRADIATION

(75) Inventors: Christoph Bert, Aschaffenburg (DE); Robert Luechtenborg, Darmstadt (DE)

(73) Assignee: GSI HELMHOLTZZENTRUM FUER SCHWERIONENFORSCHUNG GMBH, Darmstadt (DE)

( * ) Notice: Subject to any disclaimer, the term of this patent is extended or adjusted under 35 U.S.C. 154(b) by 400 days.

(21) Appl. No.: 13/512,040
(22) PCT Filed: Aug. 31, 2010
(86) PCT No.: PCT/EP2010/062737
§ 371 (c)(1), (2), (4) Date: May 25, 2012
(87) PCT Pub. No.: WO2011/064004
PCT Pub. Date: Jun. 3, 2011

(65) Prior Publication Data
US 2012/0238795 A1    Sep. 20, 2012

(30) Foreign Application Priority Data
Nov. 26, 2009   (DE) .......................... 10 2009 055 902

(51) Int. Cl.
*A61N 5/00* (2006.01)
*A61N 5/10* (2006.01)

(52) U.S. Cl.
CPC ............ *A61N 5/1048* (2013.01); *A61N 5/1043* (2013.01); *A61N 5/1067* (2013.01); *A61N 2005/1072* (2013.01); *A61N 2005/1087* (2013.01)

(58) Field of Classification Search
CPC ............. G21K 1/00; G21K 1/02; A61N 5/00; A61N 5/01; A61N 5/06; A61N 5/0601; A61N 5/0603; A61N 5/0613; A61N 5/0616; A61N 5/10; A61N 5/1001; A61N 5/1002; A61N 5/1007; A61N 5/1014; A61N 5/1045; A61N 5/1047; A61N 5/1048; A61N 5/49; A61N 5/1064; A61N 5/1065; A61N 5/1067; A61N 5/1068; A61N 5/1071

USPC ................ 250/491.1, 492.1, 492.21, 492.22, 250/492.3
See application file for complete search history.

(56) References Cited

U.S. PATENT DOCUMENTS 6,148,272 A    11/2000 Bergstrom et al.
6,409,744 B1 *   6/2002 Marchesi ........................ 607/96
(Continued)

FOREIGN PATENT DOCUMENTS

DE    102005063220 A1   6/2007
DE    102007014715 A1  11/2008
DE    102007045879 A1   4/2009

OTHER PUBLICATIONS

Krämer et al. "Treatment planning for heavy-ion radiotherapy: calculation and optimization of biologically effective dose." Phys Med Biol 2000, 45:3319-3330.
(Continued)

*Primary Examiner* — Jack Berman
*Assistant Examiner* — Jason McCormack
(74) *Attorney, Agent, or Firm* — Leydig, Voit & Mayer, Ltd.

(57) ABSTRACT

A method for controlling dosage application during irradiation of a moveable target volume in a body with an energy beam by scanning the target volume includes, before irradiating an i-th grid position, determining a dosage during the irradiation process using the movement data, wherein the dosage already contains the i-th grid position during irradiation of the previous grid positions ($1 \leq k < i$). Depending on the determined dosage that already contains the i-th grid position during the irradiation of the previous grid positions ($1 \leq k < i$), a compensation value for the i-th grid position is calculated, and depending on the compensation value and on the nominal particle fluence for the i-th grid position, a compensated particle fluence ($F^i_{komp}$) is calculated for the i-th grid position in order to irradiate the i-th grid position with the compensated particle fluence ($F^i_{komp}$).

15 Claims, 6 Drawing Sheets

(56) References Cited

U.S. PATENT DOCUMENTS

| | | | |
|---|---|---|---|
| 2006/0145088 A1* | 7/2006 | Ma | 250/396 ML |
| 2007/0034812 A1* | 2/2007 | Ma et al. | 250/492.21 |
| 2008/0226030 A1* | 9/2008 | Otto | 378/65 |
| 2009/0090870 A1* | 4/2009 | Ahnesjo et al. | 250/395 |
| 2009/0095921 A1* | 4/2009 | Bert et al. | 250/492.1 |
| 2009/0095929 A1* | 4/2009 | Lee | 251/129.15 |
| 2010/0108903 A1 | 5/2010 | Bert et al. | |
| 2010/0301235 A1 | 12/2010 | Bert et al. | |

OTHER PUBLICATIONS

Krämer et al "Treatment planning for heavy-ion radiotherapy: physical beam model and dose optimization." Phys Med Biol 2000, 45:3299-3317.

European Patent Office, International Search Report in International Patent Application No. PCT/EP2010/062737 (Aug. 31, 2010).

C. Bert et al. "4D Treatment planning for scanned ion beams.", Radiation Oncology, BioMed Central Ltd, Lo, vol. 2, Nr:1, Jul. 3, 2007, p. 1-10.

S. O. Grötzinger "Volume Conformal Irradiation of Moving Target Volumes with scanned ion beams," Technical University of Darmstadt, Germany, 2004.

C. Bert, "Bestrahlungsplanung für bewegte Zielvolumina in der Tumortherapie mit gescanntem Kohlenstoffstrahl," (Irradiation Planning for Moving Target Volumes in Tumor Therapy with a Scanned Ion Beam), Technical University of Darmstadt, Germany, 2006.

Mel and Kramer, "Treatment planning for heavy ion Irradiation", Phys. Med. 14, 1998, p. 53-62.

Lüchtenborg, R. [et al.]: On-line compensation of dose changes introduced by tumor motion during scanned particle therapy, In: Proc. of IFMBE, Sep. 7-12, 2009, p. 449-452.

Li, Q. [et al.]: Online compensation for target motion with scanned particle beams: simulation environment, In: Phys. Med. Biol. 49, 2004, p. 3029-3046.

Bert, C., Grozinger, S., Rietzel, E.: Quantification of interplay effects of scanned particle beams and moving targets, In: Phys. Med. Biol. 53, 2008, p. 2253-2265.

\* cited by examiner

Fig. 9

METHOD AND DEVICE FOR CONTROLLING DOSAGE APPLICATION DURING IRRADIATION

CROSS REFERENCE TO RELATED APPLICATIONS

This application is a U.S. National Phase application under 35 U.S.C. §371 of International Application No. PCT/EP2010/062737, filed on Aug. 31, 2010, and claims benefit to German Patent Application No. 10 2009 055 902.7, filed on Nov. 26, 2009. The International Application was published in German on Jun. 3, 2011 as WO 2011/064004 A1 under PCT Article 21 (2).

FIELD

The present invention relates to a method for controlling the dose application during irradiation of a moving target volume in a body with an energy beam, in particular with a needle-thin ion beam by means of which the target volume is scanned, and to a corresponding irradiation device.

BACKGROUND

Tumors are generally treated using resection, radiation therapy, and chemotherapy, or a combination of these methods. In radiation therapy, the aim of the treatment is to obtain a high local tumor dose while minimizing the harmful effects on the surrounding normal tissue. To this end, the energy or dose deposition is controlled to conform to the shape of the tumor to the extent possible. Recently, good therapy results have been obtained through irradiation with ions instead of photons since the energy or dose deposition as a function of the penetration depth has a sharp maximum (called Bragg peak). One such method is known as passive beam application, where the beam is shaped by a specially adapted collimator. Alternatively, however, it is also possible to focus the ion beam precisely and to scan the tumor three-dimensionally with a needle-fine beam, a so-called "pencil beam" (raster scanning method, spot scanning method, continuous scanning method). In the raster scanning method, the beam remains on at a grid position for a defined period of time and is kept on while it is shifted to the next grid position. In contrast, in the spot scanning method, the beam is switched off between grid positions. In the continuous scanning method, the beam is moved continuously over the grid positions without remaining stationary on them.

Aside from protons, other ions, especially carbon ions, are currently used. At times, neon ions are also employed. The use of these ions provides a higher relative biological effectiveness (RBE) for the inactivation of cells as compared to photons. Due to its dependence on the dose level, on the type of tissue and, above all, on the particle type and particle energy, the RBE in the deep tumor area is generally higher than in the entry channel, and thus provides an additional therapeutic benefit.

In recent years, the Applicant, in cooperation with the University of Heidelberg, the German Cancer Research Center and the Dresden-Rossendorf Research Center, has achieved considerable clinical success with raster scanning irradiation using carbon ions and dedicated radiation planning. The advantages of this method are the virtual elimination of the need for absorber materials to prevent the generation of secondary particles and, above all, the good conformity of the generated dose distributions as compared to passive beam application, especially proximal to the tumor.

Initially, the tumors mainly treated were tumors in the region of the cranial base and along the spinal column, whose motion can be reduced to a negligible minimum through stereotactic fixation. However, plans for a broader clinical application of the raster scanning method in various therapy centers envisage to irradiate also other tumors with ion beams, in particular carbon ion beams, using the raster scanning method. Tumors in the torso area of the body, however, are subject to more motion, especially due to the patient's breathing, which causes the entire rib cage and parts of the abdomen to move and change shape, and sometimes even because of the heartbeat of the patient. When moving tumors or, in general, moving target volumes are treated using a scanning method, one is faced with the challenge that this motion can have an adverse effect on the homogeneity of the energy deposition. Experiments with phantoms have shown that during application of a scanned beam, overdosage and underdosage may occur in the target volume, so that a simple enlargement of the target volume by the magnitude of the motion, as is employed in the case of passive beam application, does not allow optimal treatment.

In order to correct the influence of the motion during application of a scanned beam, at present, fractional irradiation making use of safety margins, multiple radiation (called "rescanning"), irradiation with motion-phase-dependent interruptions (called "gating"), motion-compensated irradiation with active beam adaptation (called "tracking"), or combinations of the aforementioned methods/techniques are being studied and used in pre-clinical trials. During motion-compensated irradiation with active beam adaptation (tracking), the beam position is continuously adjusted to the motion of the tumor. In this process, the lateral position of the beam with respect to the beam direction and the range of the particles are continuously adjusted to the motion of the tumor. In this connection, reference is made to the dissertation of S. O. Grötzinger "Volume Conformal Irradiation of Moving Target Volumes with scanned ion beams," Technical University of Darmstadt, Germany, 2004, and to that of C. Bert, "Bestrahlungsplanung für bewegte Zielvolumina in der Tumortherapie mit gescanntem Kohlenstoffstrahl," (Irradiation Planning for Moving Target Volumes in Tumor Therapy with a Scanned Ion Beam), Technical University of Darmstadt, Germany, 2006, both of which are hereby incorporated herein in their entirety by reference. In any case, the motion-compensated raster-scanned ion beam application is known per se to those skilled in the field of particle-beam tumor therapy.

Thus, if no countermeasures ("motion mitigation") are taken, the treatment of moving tumors with a scanned particle beam can in principle lead to dose errors due to the interaction of dynamic irradiation and moving anatomy. Even if the aforementioned methods are used, such as active beam adaptation (tracking), the path of the particle beam in the tissue may change despite the adaptation of the beam, for example when the motion of the tumor cannot be described by a pure translation. In fact, this is often the case since a motion of, for example, the rib cage may include rotational components and/or tissue deformations. Although active beam adaptation (tracking) allows the position of the Bragg peak, and thus the major portion of the particle dose, to be moved to the anatomically correct position, the change in beam path results in a change in the dose contribution to the remaining tissue, especially in the proximal region; i.e., upstream of the grid position where the Bragg peak is present. This results in local underdosage and overdosage as compared to planned dose deposition, which may be disadvantageous. In treatment simulations based on measured lung tumor data, the inventors found that, without considering the described dose changes, the dose coverage is significantly poorer as compared to simulated irradiation of a hypothetically stationary lung tumor (static irradiation, where no dose changes occur).

German Patent Application DE 10 2005 063 220 A1 describes measures for improving the time course of an irradiation which, however, are capable of being further improved with respect to the problems mentioned above.

SUMMARY

In an embodiment, the present invention provides a method for controlling the dose application during irradiation of a moving target volume in a body with an energy beam using a scanning method. The method includes creating an irradiation plan including a plurality of grid positions (i, $1<=i<=N$) of the target volume for one or more irradiation cycles (j, $1<=j<=J$). A grid-position-dependent nominal particle fluence is defined in the irradiation plan for the irradiation of each of the grid positions. A motion of the body is captured during the irradiation in order to determine a motion of the grid positions during the irradiation. The irradiation is performed by successively scanning the individual grid positions with the energy beam using a particle energy and a particle fluence that are controlled as a function of the grid position, so as to apply a grid-position-dependent dose at the corresponding grid position. The scanning includes:

i1) prior to the irradiation of an i-th grid position of the plurality of grid positions, calculating a dose that was already received by the i-th position during the irradiation of previous grid positions (k, $1<=k<i$) during the irradiation cycle using the motion data;

i2) prior to the irradiation of the i-th grid position, calculating a compensation value ($\Delta D^i$) for the i-th grid position based on the dose that the i-th grid position is determined to have already received during the irradiation of the previous grid positions (k, $1<=k<i$);

i3) prior to the irradiation of the i-th grid position, calculating a compensated particle fluence ($F^i_{comp}$) for the i-th grid position based on the compensation value ($\Delta D^i$) for the i-th grid position and a nominal particle fluence ($F^i_{nom}$) for the i-th grid position; and i4) irradiating the i-th grid position with the compensated particle fluence ($F^i_{comp}$) determined for the i-th grid position, The steps i1) through i4) are carried out for the plurality of grid positions ($1<=i<=N$).

BRIEF DESCRIPTION OF THE FIGURES

Exemplary embodiments of the present invention are described in more detail below with reference to the drawings, in which.

DETAILED DESCRIPTION

In an embodiment, the present invention provides a method and device of dose application which will improve the quality of the irradiation of a moving target volume and which, in spite of the motion, will achieve good agreement between the actual dose distribution during irradiation and a predetermined desired dose distribution.

In an embodiment, the present invention also provides a method and device of dose application which will optimize the irradiation procedure.

In accordance with an embodiment of the present invention, a moving target volume in a body is irradiated with an energy beam using a scanning method. The body may be either a living human or animal body which is irradiated to treat a tumor, or a model (animal model, cell culture, or other phantom) for validating an irradiation of a patient, or another non-living body. The beam is, in particular, a particle beam, preferably an ion beam, such as, for example, a high-energy carbon ion beam. The present invention relates in particular to controlling the irradiation device in such a manner that, for example, the aspects of beam application quality and accuracy, and also of the required computing capacity, are taken into account in spite of the motion of the target volume. In accordance with the present invention, a scanning method is used in which the target volume is three-dimensionally divided into a plurality of grid positions, and these grid positions are successively scanned by a precisely focused needle-thin ion beam. This method is known as "scanning method" to those skilled in the art. As described hereinabove, while there are always a plurality of grid positions (e.g., those located in the beam path) that receive a certain radiation dose, it will be obvious to those skilled in the art that the term "irradiation of the i-th grid position" refers to the position where the Bragg peak is placed; i.e., the grid position that receives the largest dose. Thus, in the scanning method, the accelerator control device controls the ion beam in such a way that the individual grid positions are successively scanned by the ion beam with a particle energy and a particle fluence (number of particles per unit area) that are controlled as a function of the grid position, so that a grid-position-dependent dose is applied at the corresponding grid position. The present invention is suitable, in particular, for the raster scanning method and the spot scanning method described in detail in the introduction.

In these scanning methods, initially, the time-resolved structure of the body to be irradiated and, more specifically, of the target volume (e.g., a tumor), is recorded under the influence of the body's motion, which may be caused, for example, by breathing. The recording is done prior to irradiation, using a diagnostic system capable of time-resolved three-dimensional imaging, such as, for example, a time-resolved three-dimensional computed tomography system (known as 4D-CT), a time-resolved three-dimensional magnetic resonance tomography system (known as 4D-MRT), or a time-resolved three-dimensional positron emission tomography system (known as 4D-PET). In this connection, the following procedure may be used:

1) performing a 4D-CT scan (i.e., a plurality of 3D-CT scans (motion phases M) which are ordered in time in the breathing cycle by temporal correlation with a motion surrogate)

2) if necessary, performing a 4D-MRT/4D-PET scan (segmentation, staging)

3) defining a reference motion phase, especially during exhalation 4) registering the M-1 motion phases to the reference motion phase by (non-rigid) transformations (optimization process whereby, for example, the so-called "normalized mutual Information" is minimized). The resulting M-1 transformations (and their inverses) are capable of describing the 3D motion of the tumor 5) optimizing a quasi-static reference irradiation plan using the (three-dimensional) reference phase of the 4D-CT scan and the segmented volumes (tumor and organ at risk (OAR)) from the (4D)-MR scan or from the contrast CT scan or 4D-CT scan This is generally know to those skilled in the art, for example, from Kramer et al "Treatment planning for heavy-ion radiotherapy: physical beam model and dose optimization." Phys Med Biol 2000, 45:33299-3317, Krämer et al. "Treatment planning for heavy-ion radiotherapy: calculation and optimization of biologically effective dose." Phys Med Biol 2000, 45:3319-3330, Jäkel and Krämer, "Treatment planning for heavy ion Irradiation", Phys. Med. 14 53-62

6) combining the reference irradiation plan, transformation parameters and 4D-CT phases so as to determine adaptation parameters dx, dy, dE for all grid points and all phases 7) determining the dose contributions of grid point i to grid point k as a function of motion phase m, hereinafter designated $D_m^{ik}$ 8) starting the irradiation using the irradiation method which is described in more detail below Prior to irradiation, the so-called irradiation plan is generated, as is known to those skilled in the art, using an irradiation planning device including a computer. To this end, a data tuple including at least four elements, namely, x-position, y-position, particle energy and particle fluence, is generated for each grid position for one or more irradiation cycles in a motion-phase-resolved manner. Due to the multitude of grid positions and the complexity of the problem, the generation process may take a relatively long time, which is why the irradiation plan is typically generated and stored as a whole, sometimes several hours or days prior to irradiation. In previously known methods, the patient is typically irradiated using the values from the predetermined irradiation plan.

Based on the 4D data, it is possible to determine (non-rigid) transformations; i.e. motion data, between the individual motion phases using registration algorithms known to those skilled in the art (see the description under 4 above). In other words, based on the 4DCT motion phases, a plurality of time intervals are defined in which the transformation of the parameters into the reference motion phase is determined and stored in the form of position adaptation parameters. These time intervals may be identical to the intervals defined by the (M-1) motion phases. It is also conceivable to introduce additional time intervals. Thus, the motion phases are obtained from the 4D-CT/4D-MRT data. The registration then optimizes a transformation, for example, to change from exhalation to inhalation.

Based on this data, during an irradiation performed later, the grid positions of the target volume that are actually hit by the Bragg peak under the influence of motion can be determined in real-time on the basis of a motion measurement of the body. The compensation parameters made available then make it possible to hit the "right" position.

In accordance with an embodiment of the present invention, an irradiation plan is also generated prior to irradiation. In this connection, the data set from the data tuples corresponds to a reference data set in which the particle fluence of the irradiation plan corresponds to a nominal particle fluence which will later be changed in real-time during irradiation according to the course of the irradiation. Thus, an irradiation plan including a plurality of grid positions i, $1<=i<=N$ of the target volume is generated and stored, the irradiation plan including, for the irradiation of each of the grid positions i, a reference data set containing the position data of the respective grid position and a grid-position-dependent nominal particle fluence.

During irradiation, the motion of the body is continuously captured by a motion sensing device to determine which motion phase is present at any time during the irradiation. On this basis, the actual motion of the grid positions can be determined continuously and three-dimensionally during the irradiation based on the position adaptation parameters obtained, for example, from the 4D-CT or 4D-MRT examination.

For this purpose, a computing device, during the irradiation, reads out the data sets that were stored prior to the irradiation, and changes said data sets in real-time so as to immediately subsequently perform irradiation with the changed values, in particular with a changed particle fluence.

Typically, an irradiation plan includes N grid positions, where the number N can be from several thousands to several tens of thousands, or even higher. In accordance with an embodiment of the present invention, and as will be described in greater detail hereinbelow, the actually deposited particle fluence that was received by the i-th grid position during irradiation of the other, previously irradiated k-th grid position $1<=k<i$ in the motion phase determined during the irradiation of grid position k is determined and processed for each i-th grid position $1<=i<=N$. In order to be able to perform these calculations on-line; i.e., in real-time, the following steps i1) through i4) are carried out for each i-th grid position, where $1<=i<=N$. On the other hand, the irradiation of a grid position typically takes only few milliseconds. Thus, it is obvious that a high computing power is required because of the multidimensionality of the data.

i1) The dose that was already received by the i-th position during the irradiation of the previous grid positions ($1<=k<i$) is calculated by the computing device in real-time during the irradiation cycle using the motion data and the previously (i.e. off-line) created database which contains the mutual dose contributions.

i2) After step i1), and specifically immediately prior to the irradiation of the i-th grid position, a compensation value for the i-th grid position is calculated by the computing device based on the dose that the i-th grid position is determined to have already received during the irradiation of the previous grid positions ($1<=k<i$).

i3) After i2), and still immediately prior to the irradiation of the i-th grid position, a changed data tuple with compensated particle fluence Ficomp is calculated for the i-th grid position based on the compensation value for the i-th grid position and the reference data tuple with the nominal particle fluence Finom defined for the i-th grid position in the irradiation plan.

i4) After that, the i-th grid position is irradiated with the compensated particle fluence Ficomp, which is calculated in real-time.

Sufficient dose coverage can be achieved in spite of the motion of the target volume, and local deviations from the desired values can be reduced, which makes it possible to reduce the influence of the motion on the actually deposited dose distribution.

In particular, the calculation of the compensation value for the i-th grid position is carried out during the irradiation of the i-1-th grid position.

Preferably, during the irradiation, the dose changes received by the i-th grid position during the irradiation of all previously irradiated grid positions k are summed over all k<i, and the compensation value for the irradiation of the i-th grid position is calculated during the irradiation of the i-1-th grid position from the sum of the dose changes (difference between the actual dose and the reference dose).

In accordance with a preferred embodiment of the present invention, the compensation value for the i-th grid position is calculated by the computing device as a relative correction factor in which the summed dose changes received by the i-th grid position during the irradiation of all previous k-th grid positions are normalized with a specific reference dose for the i-th grid position, so that the compensation value is a dimensionless correction factor. This compensation factor is stored in a subsystem of the therapy control system, namely, the subsystem for controlling the particle fluence, called SKT, prior to the irradiation of the i-th grid position, and subsequently, but still prior to the irradiation of the i-th grid position, loaded from the memory of the subsystem for controlling the particle fluence as the compensation value for the i-th grid position and multiplied in real-time by the nominal particle fluence defined for the i-th grid position in the irradiation plan, so as to calculate the compensated particle fluence (Fi-comp) for the i-th grid position, with which the irradiation is then performed. This advantageously makes the compensation value independent of daily changing calibration factors, which are due, for example, to the dosimetry.

Preferably, the subsystem for controlling the particle fluence SKT controls the applied particle fluence for all grid positions, and the computing device stores the compensation value for the i-th grid position during the irradiation of the i-1-th grid position in the memory of the subsystem for controlling the particle fluence SKT, so that the compensation value for the i-th grid position may be loaded from the memory by the subsystem for controlling the particle fluence immediately prior to the irradiation of the i-th grid position. Subsystem SKT then applies the compensation value in real-time to the nominal particle fluence defined for the i-th grid position in the irradiation plan, so as to subsequently irradiate the i-th grid position with the compensated particle fluence for the i-th grid position.

If, at the planned start of the irradiation of the i-th grid position, the compensation value for the i-th grid position is not yet stored in the memory of the subsystem, it would be possible to vary the beam intensity or introduce a beam pause, at least until the compensation value for the i-th grid position is stored, so as to prevent the i-th grid position from being irradiated with an incorrect particle fluence.

During the irradiation of the i-th grid position, the dose changes are not calculated for all of the subsequent grid positions o, i<o<=N simultaneously, but instead the dose change and the compensation value are preferably initially calculated only for i+1-th grid position, so as to optimally utilize the computing power and ensure that the compensation value is available as early as possible. The calculation of the dose changes and compensation values for the subsequent grid positions i+1<o<=N is not performed until the compensation value for the i-th grid position is stored in the memory of the subsystem.

Alternatively, it may be expedient to calculate, during the irradiation of the i-th grid position, the dose changes for the grid positions of the iso-energy layer in which the i-th grid position is located, and to calculate the dose changes for the grid positions of the subsequent iso-energy layers during a beam pause (so-called "spill pause") between the irradiation of the iso-energy layers.

It may happen that, during the irradiation of the previous k-th grid positions, the i-th grid position already received a dose change which is already greater than or equal to the reference dose defined for the i-th grid position in the irradiation plan. In this case, the irradiation of the i-th grid position is either skipped or carried out with a minimum dose determined prior to the irradiation. The latter may be advantageous for the continued control of the beam position. For this purpose, the minimum dose should preferably be greater than or equal to 1% of the reference dose, and preferably smaller than or equal to 30% of the reference dose.

Moreover, it is advantageous to adjust, during the irradiation, the intensity of the beam in a grid-position-dependent manner to the particle fluence to be applied to the respective grid positions. This makes it possible to equalize the irradiation times of the grid positions, so that the time available for calculating the compensation is balanced as much as possible and/or approximated to the minimum, so as to achieve an irradiation that is as fast as possible and, therefore, has a low error rate and is gentle.

Typically, the irradiation of an iso-energy layer is carried out with a beam packet (so-called "spill"), and the next iso-energy layer is irradiated only with the next beam packet (spill). In this regard, it is advantageous to define a quality index Q, on the basis of which the start of the next beam packet (spill) is automatically synchronized with an optimal motion phase. To this end, the computing device calculates the grid-position-dependent distribution of the particle fluences for the subsequent grid positions of the next beam packet (spill) for different motion phases, and automatically evaluates the synchronization by means of the quality index, for example, based on the following evaluation criteria:

Preferably, at least one of the following evaluation criteria, or a (possibly weighted) combination of these criteria, is included in the quality index Q:

i) the similarity of the compensated particle fluences of the grid positions. The advantage of this is that the irradiation times of the grid points become as similar as possible, so that this is also true for the available computing time.

ii) the deviations of the compensated particle fluences from the particle fluences of the reference doses are as small as possible. Thus, interference effects may be reduced, if necessary.

iii) potential overdoses to the subsequent grid positions are reduced. This makes it possible to achieve for each grid position a dosage as close as possible to the reference value.

iv) the time until the associated motion phase is expected to be reached. Typically, the average irradiation time of a grid position is in the range of milliseconds, that of a layer is in the range of seconds, and that of a fraction is in the range of minutes. Therefore, the motion phases may be significantly longer than the time for irradiating a grid position. Thus, if the start of the irradiation with the next beam packet (spill) is delayed too long, then this may be an additional weighting factor for the quality index.

The present invention may be combined with active adaptation of the beam to motion (tracking), but it is also a less complex alternative. In one preferred use of the present invention, active beam adaptation (tracking) is performed laterally, but not longitudinally. This means that the grid-positiondependent compensation values are determined based on the motion phase determined by measurement of a motion surrogate and the parameters determined during irradiation planning. However, only the lateral beam position is actively adapted, which is accomplished relatively easily using scanning magnet pairs. In contrast, the beam energy is not actively adapted, but, instead, the method compensates for the absence of active adaptation in the longitudinal dimension.

The effect of embodiments of the present invention can be further enhanced by combining it with an irradiation performed in multiple cycles similar to the multiple irradiation technique, where the grid positions in one fraction are scanned multiple times in succession (rescanning). Thus, in each irradiation cycle, irradiation is performed with a fraction of the reference dose. In this method, the dose changes received by the i-th grid position in the previous irradiation cycles and those received by the i-th grid position during the irradiation of the previous grid positions in the current irradiation cycle can be taken into account in the calculation of the compensation factor for the i-th grid position in an irradiation cycle. In this manner, the actual dose distribution can be even better adapted to the desired dose distribution. For example, the number of irradiation cycles can be optimized in advance based on collective data and the motion parameters, or be patient-specific, or be determined during the irradiation, for example, by accepting a dose error tolerance of 0.1% or 1% or 10% of the planned dose per fraction. Once the tolerance falls below this value, the irradiation is terminated. Other decisive factors for termination may be technical boundary conditions, such as the ability to irradiate an inhomogeneous grid (a plurality of isolated grid points per iso-energy layer).

Figure 1:
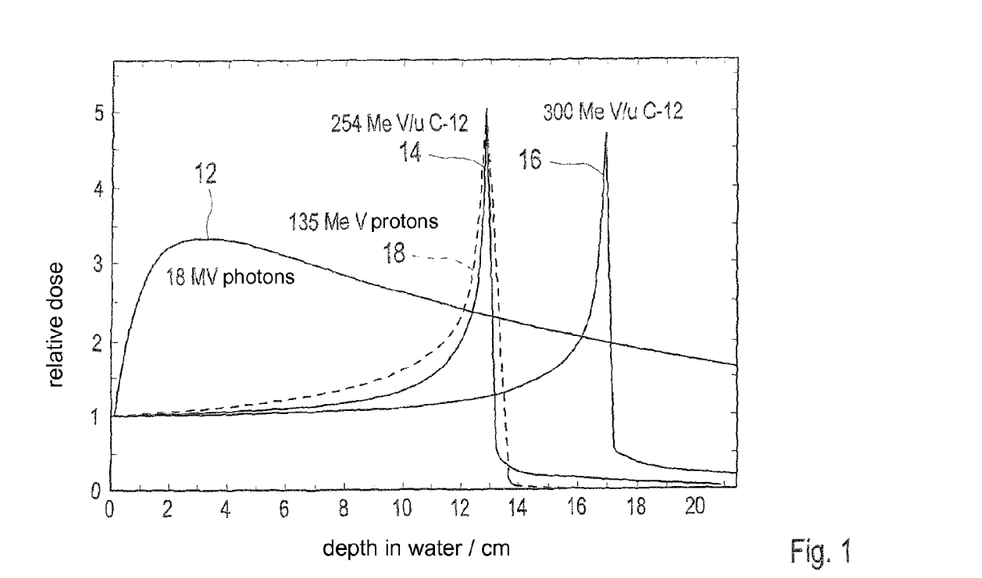
FIG. 1 is a plot showing the relative dose as a function of the penetration depth for different beam types and energies.

Referring to FIG. 1, there is shown the depth dose distribution for different types of beams. In contrast to photons (curve 12) which, after a build-up effect, exhibit an exponential drop of the dose with the depth, ions exhibit a pronounced dose maximum, which is referred to as a Bragg peak or Bragg maximum, at the end of the beam range. This maximum can be shifted in depth by varying the energy. It can be seen that the Bragg peak is sharper for carbon ions (curves 14 and 16) than it is for protons (curve 18).

Figure 2:
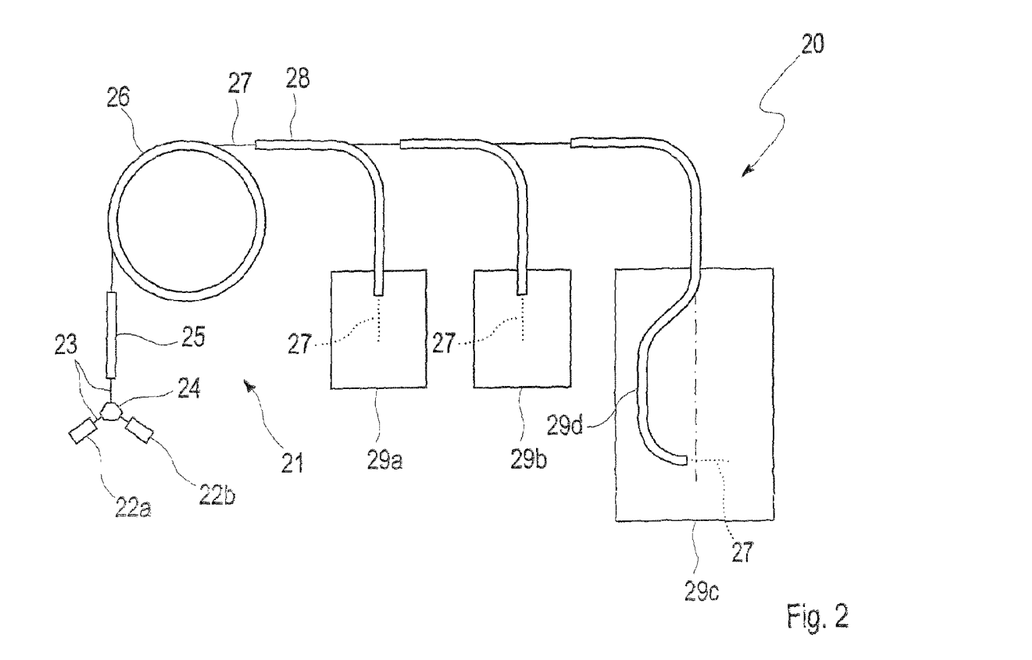
FIG. 2 is a schematic view of an irradiation device including an accelerator and three irradiation stations.

FIG. 2 is a schematic overview of the design of an exemplary irradiation device 20 for irradiating a target volume in a body. The irradiation device includes an accelerator 21 which, in this example, has two particle or ion sources 22a, 22b which generate different types of ions and whose low-energy intermediate ion beam 23 is injected by a switching magnet 24 into a linear pre-accelerator 25. Intermediate ion beam 23 is pre-accelerated by linear pre-accelerator 25 and injected into a circular accelerator 26, such as, for example, a synchrotron. Alternatively, it is also possible to use a cyclotron, a so-called "dielectric wall accelerator", or a laser-based accelerator. Some accelerators can even be installed directly in the irradiation room, for example, on a gantry, so that no separate beam guidance system is needed.

Circular accelerator 26 finally accelerates the ions to a desired energy equal to or slightly higher than the treatment energy. Ion beam or treatment beam 27 is then extracted from circular accelerator 26 and directed by beam guiding means 28 into irradiation chambers 29a, 29b, 29c, in each of which a body 30 can be irradiated with ion beam 27. For irradiation with carbon ions, the particle energy of treatment beam 27 is in a range from about 80 to 500 MeV/u. In the two left irradiation chambers 29a, 29b, target volume 32 in body 30 is irradiated substantially in the direction in which ion beam 27 enters irradiation chamber 29a, 29b. Right irradiation chamber 29c is provided what is called a rotary gantry 29d, which allows target volume 32 to be irradiated from different directions (isocentric irradiation). Body 30 may, for example, be a patient, and target volume 32 may be a tumor to be irradiated for therapeutic purposes. However, the body may also be a phantom for validating a tumor irradiation, and the target volume may, for example, be a detector or a different material to be irradiated.

Figure 3:
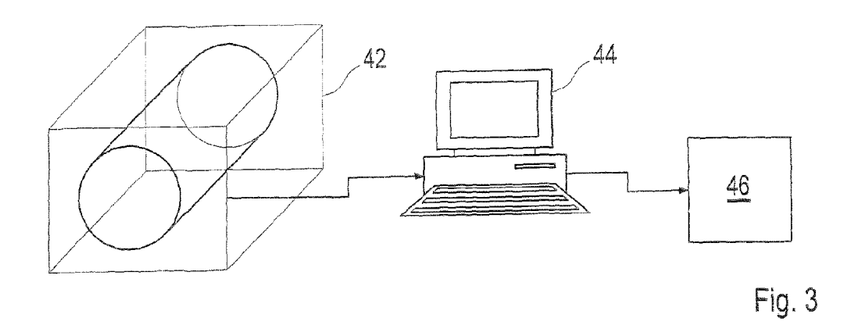
FIG. 3 is a schematic view of a system for determining the position adaptation parameters.

FIG. 3 shows a time-resolved three-dimensional imaging tomography system 42, for example, a so-called 4D-CT system or a so-called 4D-MRT system, including motions sensors and a computing device. The tomography system records the 3-dimensional motion of target volume 32, for example, of the tumor, under the influence of the motion of body 30, for example, the breathing of the patient, and divides the motion data into M motion phases. Then, prior to the irradiation, computer 44 generates an irradiation plan 46 based on the total desired dose to be deposited, the irradiation plan containing the position and nominal particle fluence data for each grid position to be irradiated.

In addition, computer 44 creates a position adaptation table containing three-dimensional position adaptation parameters ($\Delta xi$, $\Delta yi$, $\Delta Ei$) for each of the motion phases m ($1 \leq m \leq M$), so that, based on this position adaptation table and knowing the motion of the body, it is possible to calculate the actual position of each individual grid position and/or the deviation of the actual position from a reference position in a reference motion phase m=ref. In this connection $\Delta xi$ stands for the deviation of the lateral x-position of grid position i in motion phase m from the x-position of grid position i in reference phase m=ref. Analogously, $\Delta yi$ defines the deviation in the other lateral direction, namely, in the y-direction. $\Delta Ei$ defines the deviation of the ion energy to shift the Bragg peak from the reference position of grid position i to its actual position; i.e., the longitudinal position adaptation parameter.

Figure 4:
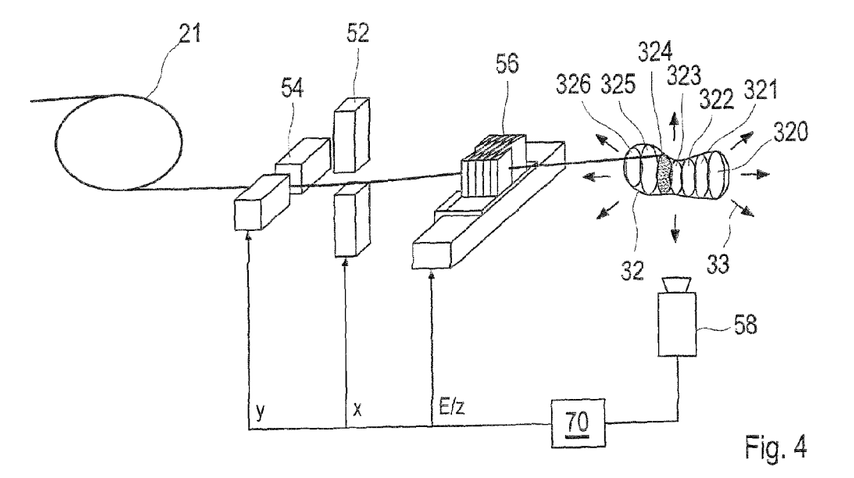
FIG. 4 is a schematic view of a device for three-dimensional active beam adaptation (tracking)

FIG. 4 is a simplified schematic view illustrating an irradiation with active motion compensation. Accelerator 21 provides treatment beam 27, which is scanned laterally across target volume 32 by means of two pairs of scanning magnets 52, 54. The target volume is divided into a plurality of iso-energy layers, here 318-324, which are scanned successively. It is generally expedient to perform scanning from the distal to the proximal iso-energy layers; i.e., to begin with the highest energy. At the instant illustrated in FIG. 4, iso-energy layer 322 is being laterally scanned. If target volume 32 moves, as symbolized by arrows 33, and the motion of the currently irradiated grid position i is known, then the beam position is actively adapted to the motion of target volume 32, laterally by means of scanning magnets 52, 54 and longitudinally by means of a double wedge system 56, in order to hit the intended grid position i in spite of the motion of target volume 32. The actual position of the currently irradiated grid position i is determined by means of motion sensing device 58, which captures the motion of body 30, and the position adaptation table stored in therapy control system 70.

Figure 5:
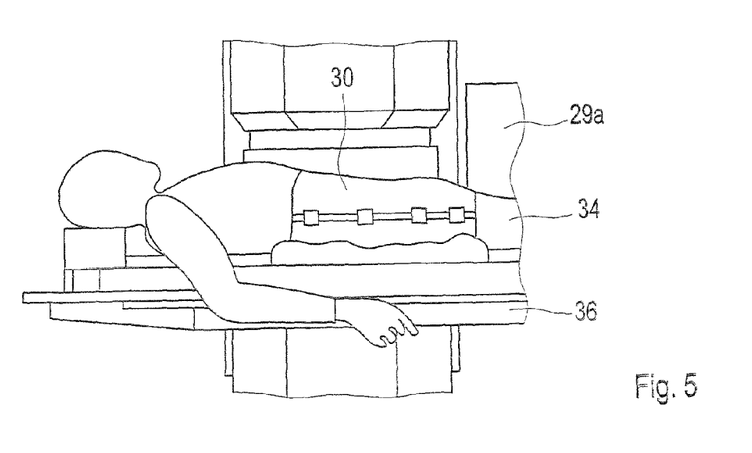
FIG. 5 is a view of a patient to be irradiated in the irradiation station.

FIG. 5 shows a patient 34 on a patient table 36, for example, in irradiation chamber 29a. Alternatively, a different body 30, such as a phantom, may be irradiated instead of live patient 34.

Figure 6A:
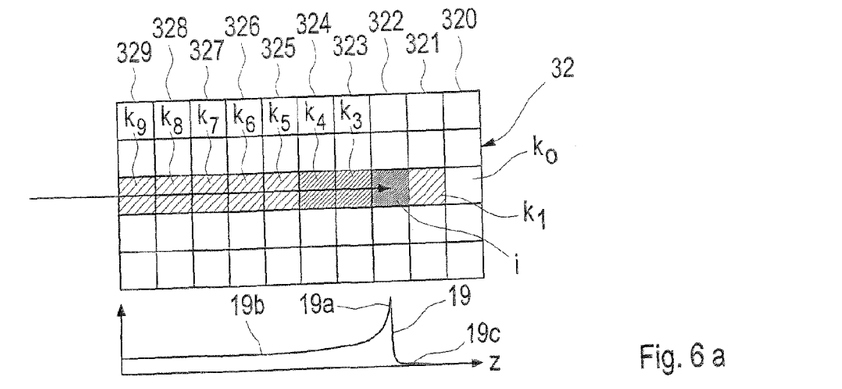
FIG. 6a is a schematic view illustrating the irradiation of a beam position with a needle-thin ion beam.

In FIG. 6a, grid position i is currently to be irradiated. This means that the beam is directed laterally (x, y) to grid position i, and particle energy (E) is selected such that the Bragg peak is located in iso-energy layer 322, in which current grid position i is located. To this extent, FIG. 6a illustrates the irradiation of a stationary target volume 32.

From the dose deposition 19 as a function of penetration depth z, it is obvious that, despite the sharp Bragg peak 19a, dose depositions are also received by grid positions other than grip position i, in particular by the grid position in the plateau region 19b upstream of Bragg peak 19a in the beam path, but to a lesser extent also by the positions on the beam axis downstream of Bragg peak 19a of [sic. at] grid position i, that is, in region 19c behind Bragg peak 19a. These dose depositions in the other grid positions k0, k1 and k3 through k9 in a stationary target volume 32 are already taken into account in ("static") reference irradiation plan 46. Specifically, the irradiation plan 46 generated prior to the irradiation contains a table which defines the number of particles to be deposited at each grid position in order to achieve a predetermined dose deposition for each grid position. The dose deposition received by grid position i during the irradiation of all other grid positions k, for example due to the plateau 19b upstream of Bragg peak 19a, is already taken into account in this irradiation plan 46, but under the assumption that target volume 32 is stationary.

Figure 6B:
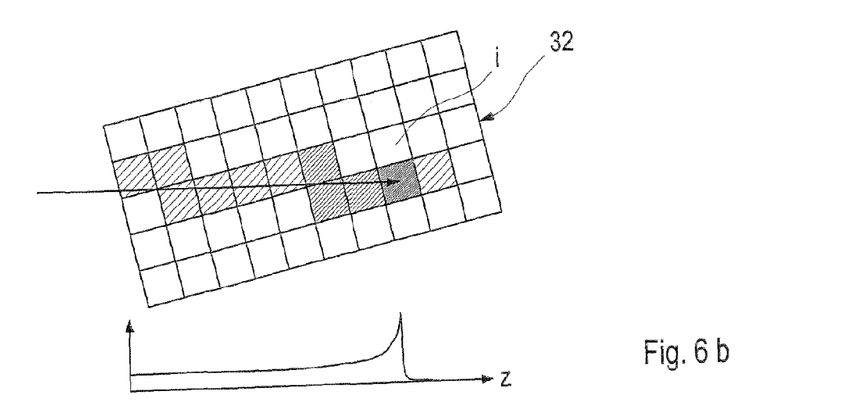
FIG. 6b is a schematic view illustrating the irradiation of a beam position with a needle-thin ion beam under the influence of motion.

If the target volume moves, as shown, for example, in FIG. 6b, so that the grid position i that is actually intended to be irradiated moves upward and, in addition, the target volume is tilted, then this results in two negative effects, namely, firstly, the Bragg peak no longer hits the grid position i that is actually intended to be irradiated and, secondly, the beam path through target volume 32 changes, for example, due to the tilting of the target volume. Moreover, target volume 32 may also deform, which also changes the beam path.

Figure 6C:
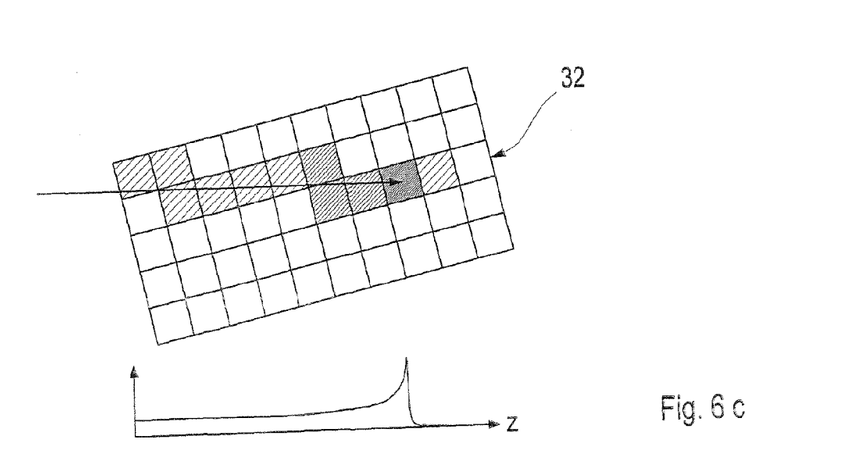
FIG. 6c is a schematic view illustrating the irradiation of a beam position with a needle-thin ion beam under the influence of motion after active beam adaptation.

Through active adaptation of the beam position, it is possible to cause Bragg peak 19a to be shifted back to grid positions [sic. grid position] i, as shown in FIG. 6c. This method of actively adapting beam 27 is generally known and referred to as "tracking" by experts in the field. Yet, as can also be seen in FIG. 6c, the beam takes a different path through the target volume than that in the irradiation plan created under the assumption of a stationary target volume according to FIG. 6a, so that the dose deposition, for example of plateau region 19b, takes place in other grid positions k than in the case of a stationary target volume even though the beam is actively adapted to the motion of target volume 32. These deposition errors cannot be eliminated by active adaptation of beam 27 alone, and they are not taken into account in static irradiation plan 46. This is where the present invention comes into play.

In the following, the present invention is described with reference to individual grid positions, which are denoted by variables such as i, k or other placeholders in order to relate them to one another. It is obvious that these placeholders are used as variables to refer to all grid positions, such as, for example, 1<=i<=N.

Figure 8:
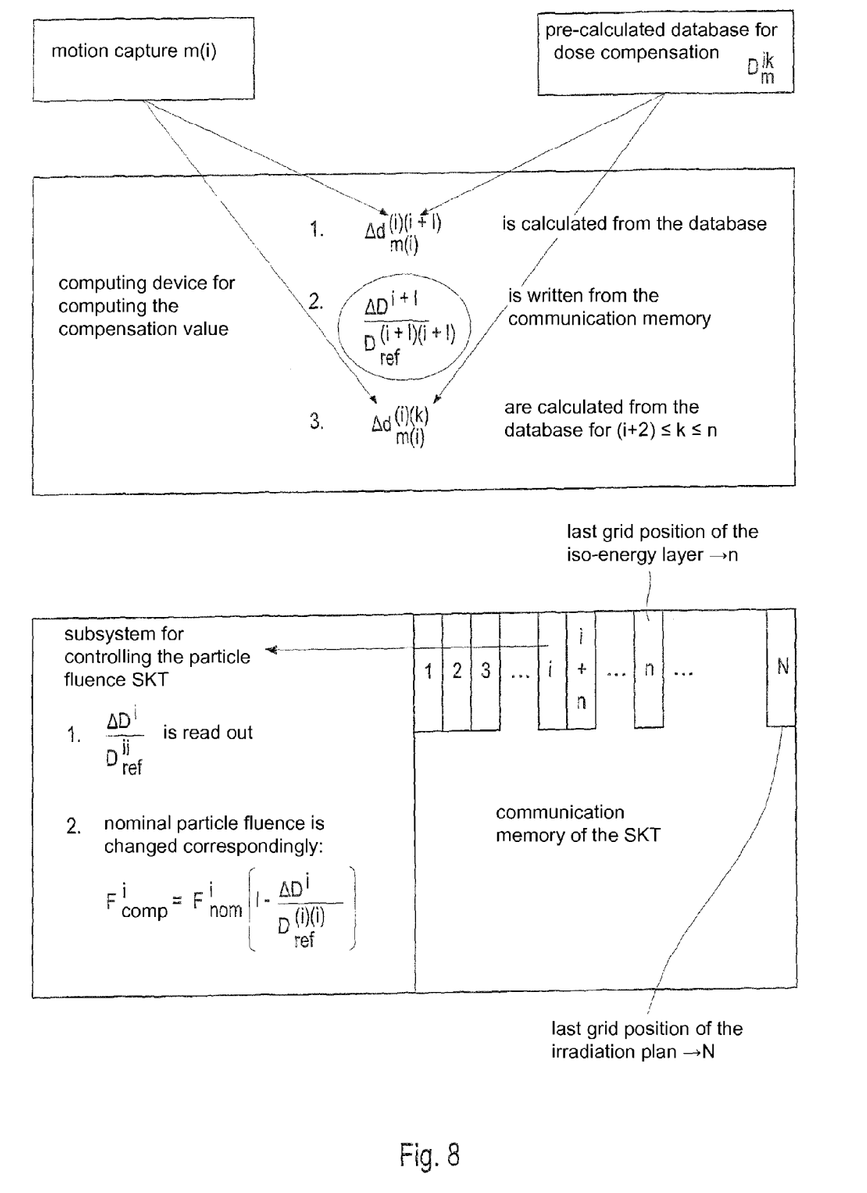
FIG. 8 is a diagram illustrating the calculation of the compensation value.

The irradiation plan is composed of N grid position and includes M motion phases. Referring to the diagram shown in FIG. 8, the dose deposited at grid position k during the irradiation of grid position i in motion phase m is pre-calculated prior to irradiation and denoted by $D_m^{ik}$. In this connection, it is assumed that at grid position i, a dose is deposited which is in accordance with the irradiation plan. For each grid position i, these values are calculated prior to irradiation for all grid positions k still to be irradiated and for all possible motion phases 1<m<M. As described with reference to FIG. 4, irradiation is generally performed from distal to proximal, so that changes occurring proximally during the irradiation of distal grid positions may be corrected during the subsequent irradiation of the proximal grid positions.

During the irradiation of a grid position i, the thereby caused dose changes $\Delta d_{m(i)}^{ik}$ of all subsequently irradiated grid positions k (at which the dose can still be actively changed) are calculated according to the present invention as a function of the motion of each individual grid position, using the following equation:

$$\Delta d_{m(i)}^{ik} = \left( D_{m(i)}^{ik} \left( 1 - \frac{\Delta D^i}{D_{ref}^{ii}} \right) - D_{ref}^{ik} \right), \tag{1}$$

where m(i) denotes the measured motion phase during the irradiation of grid position i and $\Delta D^i$ denotes the dose change accumulated for grid position i up to this point in the course of the irradiation, the accumulated dose change being calculated in real-time during irradiation by summation of the individual contributions of all previously irradiated grid positions to grid position i:

$$\Delta D^i = \sum_{l=0}^{i-1} \Delta d_{m(l)}^{li}. \tag{2}$$

Thus, $\Delta D^i$ relates to the dose change at grid position i, which can be used as a compensation value.

In the term $$\frac{\Delta D^i}{D_{ref}^{ii}}$$

in formula (1), the accumulated dose is normalized to the dose $D_{ref}^{ii}$ which grid position i is intended to receive during the irradiation of grid position i according to the irradiation plan. Index "ref" stands for reference phase m=ref. The actual instantaneous position of each grid position in each motion phase m can be calculated based on the position adaptation table created (off-line) prior to the irradiation during irradiation planning.

Figure 7:
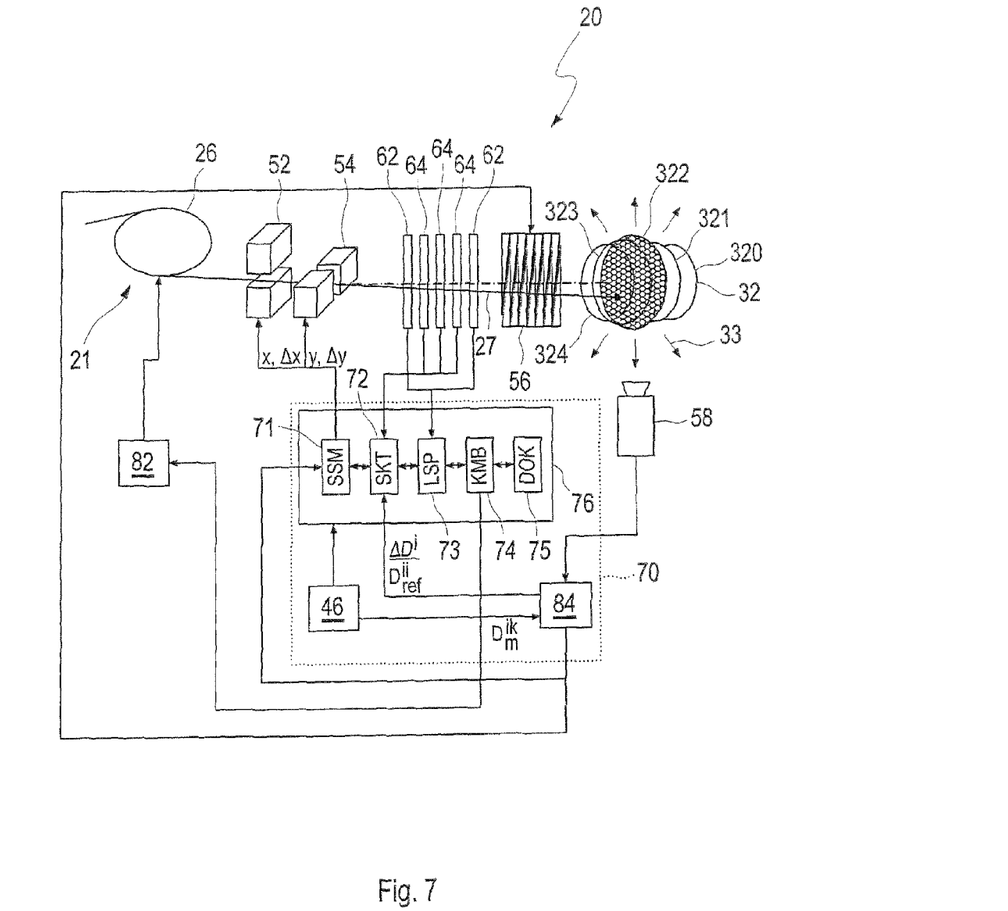
FIG. 7 is a schematic view showing the irradiation device with control elements.
Figure 9:
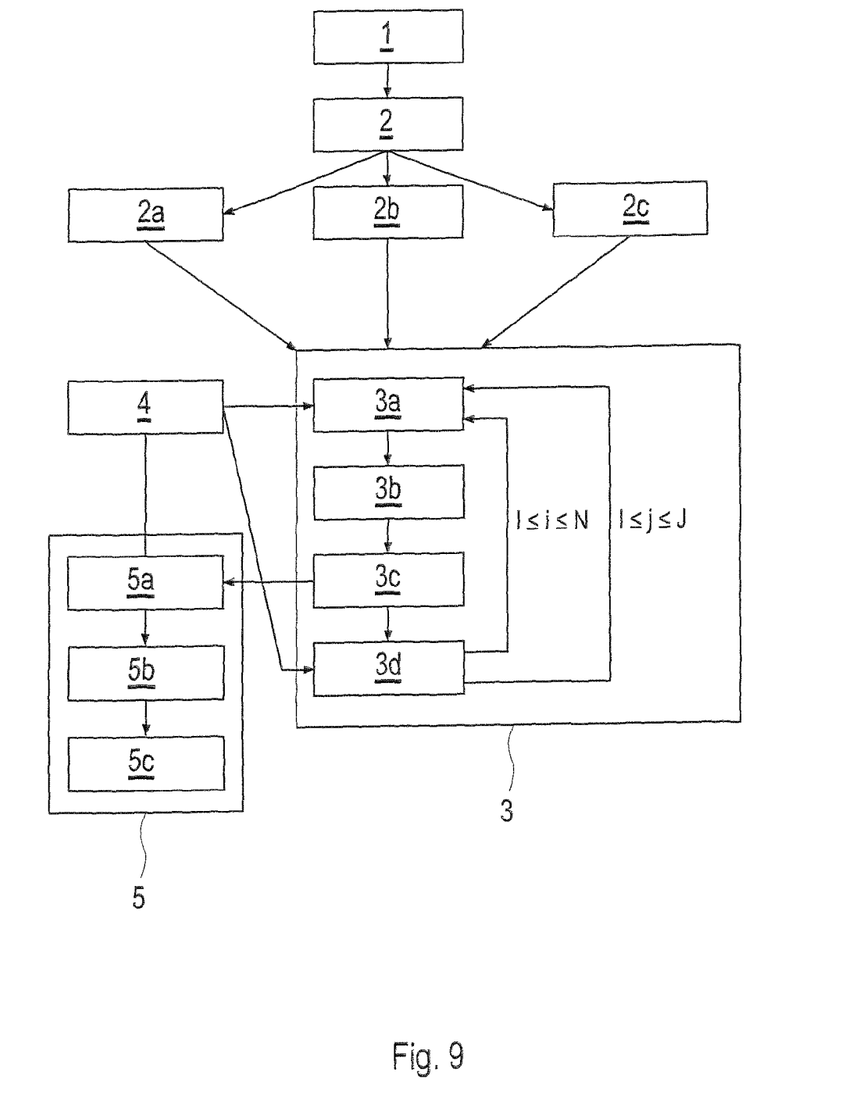
FIG. 9 is a flow chart for the calculation of the compensation value.

During the irradiation of grid position i, the normalized, and thus relative, dose change of the next grid position $$\frac{\Delta D^{i+1}}{D_{ref}^{(i+1)(i+1)}}$$

is transmitted to the subsystem for controlling the particle fluence (SKT) 72 (see FIGS. 7 and 9). In the irradiation control system, the communication memory of SKT 72 is used for this purpose, which is accessible from both SKT 72 and from all other subsystems 71, 73, 74, 75 while an irradiation is in progress. Other accelerators may also use other communication protocols and devices capable of real-time communication.

The use of the dimensionless relative dose change $$\frac{\Delta D^i}{D_{ref}^{ii}}$$

as a compensation value advantageously allows SKT 72 to apply the dose change without the need to convert dose units into machine parameters. In addition, this relative quantity is independent of daily changing calibration factors of the ionization chambers 64 used for dose monitoring.

However, instead of relative dose changes, it is also possible to convert the dose change $\Delta D^i$ into the corresponding unit (machine parameter) of the SKT and transmit this absolute quantity.

The nominal particle fluence $F^i_{nom}$ from the irradiation plan is multiplied by the compensation factor $$\left(1 - \frac{\Delta D^i}{D^{ii}_{ref}}\right);$$

i.e., the particle fluence $$F^{i+1}_{comp} = F^{i+1}_{nom}\left(1 - \frac{\Delta D^{i+1}}{D^{(i+1)(i+1)}_{ref}}\right)$$

which is compensated by the accumulated dose change is then applied for the next grid position i+1.

Thus, the compensated particle fluence reflects exactly the dose contribution that is still needed in order for grid position i+1 to receive at least the reference dose defined in the irradiation plan, and to do so despite the motion and despite the change in the beam path. Accordingly, the compensation factor in formula (1) reflects that the irradiation of grid position i is not performed with the reference dose, but with a dose that is changed by the compensation factor $$\left(1 - \frac{\Delta D^i}{D^{ii}_{ref}}\right).$$

Referring to the flow chart shown in FIG. 9, the procedure is as follows:

Block 1: A time-resolved tomography scan (a so-called 4D diagnostic scan such as, for example, a 4D CT scan) is performed, or time-resolved tomography data is calculated based on a 3DCT scan and patient-specific or population motion data.

Block 2: Prior to irradiation, irradiation planning is carried out taking into account the motion phases m (so-called 4D irradiation planning) based on the data of the time-resolved tomography scan according to the following procedure:

Block 2a: Data tuples (xi, yi, Ei, Ti) are defined for each grid position 1<=i<=N, where xi and yi are the lateral positions, Ei is the particle energy, and Ti is the number of particles to be deposited at the i-th grid position. It is obvious that the number of particles and the particle fluence are exchangeable quantities. The definition is carried out prior to irradiation for one or J irradiation cycles with N grid positions each, and the result is generally referred to as irradiation plan.

Block 2b: Position adaptation parameters are defined for each grid position i and for each motion phase m ($\Delta$xi, $\Delta$yi, $\Delta$Ei) based on the data of the time-resolved tomography, which allows the actual location of the grid positions upon motion to be calculated back to a reference position which, in reference phase m=ref, corresponds to a hypothetical state of rest.

Block 2c: Dose compensation parameters $D_m^{ik}$ are defined for all combinations i,k=1 . . . N and all motion phases m=1 . . . M.

To this end, the following steps are carried out:

if necessary, performing a 4D-MRT/4D-PET scan (segmentation, staging);

defining a reference motion phase, especially during exhalation;

if no 4D-CT scan is available, performing a 4D-CT scan;

registering the M-1 motion phases to the reference motion phase by (non-rigid) transformations (optimization process during which, for example, the so-called "normalized mutual Information" is minimized). The resulting M-1 transformations (and their inverses) are capable of describing the 3D motion of the tumor;

optimizing a quasi-static reference irradiation plan using the (three-dimensional) reference phase of the 4D-CT scan and the segmented volumes (tumor and organ at risk (OAR)) from the (4D)-MR scan or from the contrast CT scan or 4D-CT scan. This is generally know to those skilled in the art, for example, from Kramer et al "Treatment planning for heavy-ion radiotherapy: physical beam model and dose optimization." Phys Med Biol 2000, 45:3329.9-3317, Krämer et al. "Treatment planning for heavy-ion radiotherapy: calculation and optimization of biologically effective dose." Phys Med Biol 2000, 45:3319-3330, Mel and Krämer, "Treatment planning for heavy ion Irradiation", Phys. Med. 14 53-62;

combining the reference irradiation plan, transformation parameters and 4D-CT phases so as to determine adaptation parameters dx, dy, dE for all grid points and all phases;

determining the dose contributions of grid point i to grid point k as a function of motion phase m, hereinafter designated $D_m^{ik}$;

Block 3: During irradiation, steps 3a through 3d are carried out in combination with positions 4 and 5 in real-time for all grid positions over all 1<=i<=N and, if applicable, for all irradiation cycles 1<=j<=J:

Block 3a: $\Delta d_{m(i)}^{(i)(i+1)}$ is calculated based on the dose compensation parameters from block 2c and as a function of the motion data from block 4, which is captured by the motion sensing device $$\frac{\Delta D^{i+1}}{D^{(i+1)(i+1)}_{ref}}$$

Block 3b: The relative, dimensionless compensation factor is calculated.

Block 3c: The relative, dimensionless compensation factor $$\frac{\Delta D^{i+1}}{D^{(i+1)(i+1)}_{ref}}$$

is transmitted to the subsystem for controlling the particle fluence SKT and stored in the communication memory of the SKT according to position 5.

Block 3d: $\Delta d_{m(i)}^{ik}$ is calculated based on the dose compensation parameter $D_m^{ik}$ from block 2c and as a function of the motion data from block 4, which is captured by the motion sensing device, for all [grid positions] k>i+1 still to be irradiated, Block 4: The motion data is captured by the motion sensing device.

Block 5: The particle fluence is controlled by the subsystem for controlling the particle fluence SKT 72.

Block 5a: The dose change $$\frac{\Delta D^{i+1}}{D^{(i+1)(i+1)}_{ref}}$$

is read out of the memory of the SKT.

Block 5b: The compensated particle fluence $F^i_{comp}$ is calculated by SKT 72.

Block 5c: Grid position i+1 is irradiated with the compensated particle fluence $F^i_{comp}$.

Thus, in summary, a compensation value is calculated in real-time during the irradiation, and the compensation value is applied to the nominal particle fluence to obtain a compensated particle fluence, which is then used for irradiation instead of the nominal particle fluence defined in the irradiation plan. The compensation value is dependent on the dose actually applied under motion in a grid-position-specific manner, and thus is grid-position-dependent and motion-dependent.

In an embodiment, the present invention also provides a solution for controlling the time course of the relatively complex dose compensation process, namely preferably by ensuring, during the irradiation of a grid position i, that the compensation value for the subsequent grid position i+1 is transmitted to the SKT before the SKT applies the compensation value.

FIG. 7 shows an example of how the present invention may be implemented. Ion beam 27 generated by accelerator 21 is directed to target volume 32 which, here, is divided into iso-energy layers 320 through 324 and moves intra-fractionally during irradiation, as indicated by arrows 33. Beam 27 is scanned laterally; i.e., in the x- and y-directions, across target volume 32 by means of scanning magnet pairs 52, 54. At the instant shown in the figure, the beam is being scanned across iso-energy layer 322.

The actual beam position is monitored by at least one, in this example two, multi-wire chambers 62, and the position data is transmitted to the subsystem for monitoring the lateral beam position LSP 73. If the lateral position of beam 27 does not match the position according to irradiation plan 46 with sufficient accuracy, LSP 73 causes an interlock.

The subsystem for controlling the scanning magnets SSM 71 controls the scanning magnets, and thus, the lateral grid position in the x- and y-directions.

The subsystem for controlling the particle fluence SKT 72 checks the actually deposited particle number or fluence and, with the aid of ionization chambers 64, which may be three times redundant, decides on the basis of the irradiation plan 46 and based on the compensation value when the current grid position i has received enough particles and the system can switch to the next grid position i+1. The switch-over command is communicated by module SKT 72, inter alia, to module SSM 71, which then controls the scanning magnets accordingly. Module SKT 72 also communicates the end of an iso-energy layer.

The subsystem for monitoring the accelerator KMB 74 communicates with the control device 82 for accelerator 21. Via this communication, therapy control system 70 makes, for example, a request for the next beam packet (spill) with the currently required parameters including the particle energy for the current iso-energy layer, beam focus and beam intensity. Here, in addition to subsystems 71 through 74, therapy control system 70 includes also a subsystem DOK 75 for documentation, as well as irradiation plan 46 and a computing device 84.

During the irradiation of iso-energy layer 322, motion sensing device 58 captures the motion of body 30 and transmits this data to computing device 84 for calculation of the compensation value. During the irradiation of the current grid position i, computing device 84 then calculates the motion-dependent compensation value $$\frac{\Delta D^{i+1}}{D_{ref}^{(i+1)(i+1)}}$$

in real-time based on the position adaptation table created according to FIG. 3 and the ("static") reference dose compensation parameters $D_m^{ik}$. Computing device 84 obtains the dose compensation parameter $D_m^{ik}$ from irradiation plan 46. Computing device 84 transfers the motion-dependent compensation value $$\frac{\Delta D^{i+1}}{D_{ref}^{(i+1)(i+1)}}$$

for each grid position i in real-time to module SKT 72. Based on the nominal particle fluence from irradiation plan 46 and the compensation value from computing device 84, module SKT 72 calculates the compensated particle fluence in real-time and communicates with module SSM 71 so as to correspondingly control beam 27 to switch to the next grid position i+1 when the compensated particle fluence has been deposited.

In the present example, the dose compensation according to the present invention is combined with three-dimensional active beam adaptation, so that computing device 84 controls module SSM 71, and module SSM 71 subsequently controls scanning magnets 52 and 54, by providing Δx and Δy values for adapting the beam in the lateral direction. Further, computing device 84 controls double wedge system 56, which is used to perform longitudinal beam adaptation, or some other system for active energy adaptation.

In the present example, therapy control system 70 includes a VME-BUS system 76, so that modules 71 through 75 can communicate with each other via the VME-BUS bus.

Advantageous Embodiments

The present invention can be further refined as follows:

a) During the irradiation of a grid position i, instead of calculating the dose changes for all of the subsequent grid positions k>i and subsequently transmitting the accumulated compensation value for the next grid position i+1 to SKT 72 and storing it therein, initially, only the dose change contribution for the next grid position i+1 is calculated, and the accumulated compensation value for this grid position i+1 is subsequently transmitted. It is not until then that the contributions to all remaining grid positions i+2<=k<=N are calculated.

This ensures that the compensation value for the irradiation of the next grid position, here i+1, is available as early as possible in the communication memory of SKT 72.

b) During the irradiation of a grid position, only the dose changes for grid positions of the same iso-energy layer are calculated. Dose change contributions to the remaining grid positions in the other iso-energy layers of irradiation plan 46 are not processed until later during an irradiation pause (spill pause), which takes place upon completion of the iso-energy layer at the latest. This method is suitable, for example, for accelerators employing active energy variation. An example of this is an accelerator with a synchrotron, in which the beam energy that defines the iso-energy layer to be irradiated is actively varied in the synchrotron. This is associated with the generation of a new beam packet (spill), so that beam pauses occur anyway between the irradiation of the [different] iso-energy layers.

Other accelerators, such as those having a cyclotron, define the beam energy by means of absorber plates (passive energy variation). Similarly, in this case, the insertion and/or removal of the absorber plates for varying the energy is associated with a beam pause. This beam pause, too, may be used to calculate the dose change contributions to the remaining grid positions in the other iso-energy layers of the irradiation plan.

Deferring the calculation of the dose change contributions of the remaining grid positions in the other iso-energy layers shortens the computing time during the time-critical phase of successive irradiation of the grid positions within one iso-energy layer, and thus reduces the probability that the necessary calculations take longer than the irradiation of a grid position.

Optionally, if there is still not enough time to calculate the dose change contributions of all subsequent grid positions, the irradiation of the next grid positions may be delayed by interrupting the beam until the calculations are completed, or the beam intensity is reduced.

c) Further, it is advantageous to create a memory array, in which for each grid position a memory location is reserved for the compensation value. Then, the compensation value is not written to the same location in the memory for all grid positions, but instead the compensation values are written to a predefined memory location in the array for each grid position. This makes it possible that a "0" (i.e., no compensation, and thus, application of the normal particle fluence) may be read instead of the compensation value of the previous grid position i) for the irradiation of the i+1-th grid position if the compensation value for the i-th grid position is [attempted to be] read out before it is written into the memory, which may happen, for example, when there is not sufficient time for the calculation and additional pauses for the calculation are not desired. The memory array is preferably created in a communication memory of SKT 72.

d) If the accumulated dose change $\Delta D^i$ of a grid position i is greater than or equal to the desired dose $D_{ref}^{ii}$ of grid position i, then this corresponds to a relative dose change≥1. In this case, grid position i has already received an at least adequate dose during the irradiation of the previous grid positions k<i. In this case, this grid position i may be skipped, if technically possible. This may be done, for example, by briefly interrupting the beam, continuing the irradiation plan in spite of error messages during position measurement, or the like. Alternatively, however, at least a predefined minimum dose is used. The minimum does may be selected prior to irradiation, and may amount to, for example, 1%, 5%, or 30% of $D_{ref}^{ii}$. Irradiation with a minimum dose makes it possible to prevent inconsistencies in the control system. For example, this ensures that a dose deposition is also provided for this grid position, which may then be used by the multi-wire chambers to determine the lateral beam position. Moreover, by using a minimum dose, it is possible to reduce the occurrence of alternately fluctuating dose distributions at the grid positions. Namely, if a dose at grid position i that is increased compared to the reference dose results in an overdose to the adjacent grid position i+1, and the dose applied at grid position i+1 is therefore significantly reduced, then this will, in turn, result in an underdose at grid position i+2, and so on. This mutually self-reinforcing effect can be reduced by using the minimum dose.

e) If the accelerator allows the irradiation to be briefly interrupted, for example, by what is called "knockout extraction", then the beam, and thus the irradiation, may be interrupted in the event that more computing time is needed during the irradiation of a grid position.

These measures make it possible to optimize the time course of the complex calculation of the compensation factors, and to reduce the probability of errors in said time course.

The method of the present invention may be used for various irradiation methods, in particular:

2a) Single irradiation cycle
The irradiation according to the irradiation plan includes only one irradiation cycle; i.e., all grid positions are scanned only once. In this case, it is sufficient to calculate the values $D_m^{ik}$ for i<k<N prior to irradiation, because after irradiation of a grid position i, only the particle fluence of grid positions k>i can be actively changed. In this case in particular, irradiation is performed from distal to proximal.

2b) Multiple irradiation cycles
The irradiation according to the irradiation plan includes a plurality of irradiation cycles 1<=j<=J; i.e., all grid positions are scanned multiple times in succession, similar to the classical multiple irradiation technique (rescanning).

To date, however, the classical multiple irradiation technique (rescanning) has been used as an alternative to active beam adaptation (tracking) for the irradiation of moving tumors and, in such processes, the target volume is irradiated J times with 1J-th of the planned total dose at any one time (typically using extended safety margins) in order to achieve statistic averaging by multiple scanning. In accordance with the present invention, the compensation values of an irradiation cycle j preferably also take into account the dose changes of the previous irradiation cycles. For example, the compensation value for the i-th grid position in the j-th irradiation cycle is determined based on the dose changes of the i-th grid position during the irradiation of all grid positions in the previous irradiation cycles p, where 1<p<j, and based on the dose changes of the i-th grid position during the irradiation of the previous grid positions k, where 1<=k<i, in the current irradiation cycle j.

Thus, using the method of the present invention, the full planned dose may possibly be applied already during the first irradiation, while during later irradiations, only motion-related dose changes are compensated. However, it is also possible to apply fractions of the planned total dose in each irradiation cycle. This reduces the occurrence of overdosages. It is even possible to decide during the irradiation whether an additional irradiation cycle is to be carried out, or whether the already deposited dose is close enough to the planned dose. In the case of multiple irradiation cycles, the values $D_m^{ik}$ for all 1<k<N are calculated prior to irradiation, because starting with the second irradiation cycle, dose changes at grid positions k<i can also be actively changed.

The method of the present invention may further be combined with various methods for motion compensation. "Active motion compensation" is understood to mean the active adaptation of the beam to the motion of the target volume (tracking). The method of the invention may, for example, be combined with the following:

3.a) No active motion compensation.
The method of the present invention may in some cases replace active motion compensation in all three dimensions.

3.b) Longitudinal active motion compensation
Longitudinal active motion compensation (energy adaptation) is performed without lateral active motion compensation.

3.c) Lateral active motion compensation
Lateral active motion compensation (1- or 2-dimensional) is performed without longitudinal active motion compensation.

This is particularly advantageous because it is relatively complex to actively adapt the beam energy.

In the case that no full motion compensation is performed (variants 3.a) through 3.c), the Bragg peak may even be in a grid position other than that defined in the irradiation plan, so that the major portion of the dose is deposited at a "wrong" grid position. In accordance with the present invention, this is taken into account in the $D_m^{ik}$ calculated prior to irradiation. The grid position at which main part of the dose is deposited is retrieved during the irradiation from the table created for this purpose. The compensated dose change of this grid position is then applied.

In particular variant 3.c is clinically relevant, because in this variant, the technically complex energy adaptation is not used, and occurring dose changes are nevertheless compensated using a combination of lateral active motion compensation and the inventive grid-position-dependent compensation value for the particle fluence.

3.d) Three-dimensional active motion compensation

This means that the beam is actively adapted to the lateral motion of the target volume in both lateral dimensions x, y, and the beam energy is actively adapted to the longitudinal motion, for example, by means of an actively controlled double wedge system. In this case, the method of the present invention achieves an additional improvement of the irradiation for a moving target volume.

The various options available with regard to the number of irradiation cycles and the extent of the active motion compensation can be combined with one another.

3.e) The method of the present invention can be combined with gating. It is possible, for example, to take into account only a portion of the motion phases, such as, for example, 30% centered around exhalation, or all phases except for phases of unstable tumor motion.

4. Further Embodiments

Exact prediction of the tumor motion pattern with the accuracy needed for dose compensation is not possible on a long-term basis; i.e., prior to a treatment and for the entire treatment process. However, in the beam pauses (spill pauses), various methods may be used to predict the short-term motion pattern of the grid positions of the target volume and, in response thereto, improve the irradiation procedure. For a number of grid positions which are anticipated to be irradiated in the motion phase at the beginning of the next beam packet (spill), the compensated particle fluence of the grid positions is calculated, taking occurring dose changes into account. While it is generally not possible to predict the fluence distribution for several motion cycles, because the transitions between motions cycles cannot be precisely predicted due to motion variations, a prediction of the dose changes can be performed at least for several grid positions i based on possible motion phases m. Various methods may be used to improve the irradiation procedure according to technical and medical criteria.

4.a) Change of the sequence

The sequence in which the grid positions are irradiated is changed. For example, in combination with a change in intensity within the beam packet (spill), the irradiation sequence of the grid positions may be selected according to their particle fluence. This is possible, for example, in the case of knockout extraction.

4.b) The distribution of the particle fluences for the next grid positions is pre-calculated for several motion phases m and evaluated by means of a quality index Q. Accordingly, the irradiation is resumed only in the most favorable motion phase. The following evaluation criteria may be included in quality index Q:

i) the compensated particle fluences of the grid positions are as similar as possible;

ii) the deviations of the compensated particle fluences from the nominal particle fluences from the irradiation plan are as small as possible;

iii) overdoses are minimized. In this regard, while the dose in distal; i.e., already irradiated grid positions, cannot be actively changed anymore, it is still possible to reduce, or even prevent, potential overdoses at proximal; i.e., subsequently irradiated grid positions. Potential overdoses may also be differently weighted by weighting factors;

iv) The time until the associated motion phase is expected to be reached.

4.c) In accordance with a preferred embodiment, the beam intensity is adjusted in response to the particle fluence in a grid-position-dependent manner. In particular, grid positions with low particle fluence are irradiated with low intensity, and grid positions with high particle fluence are irradiated with high intensity. This results in equalization of the irradiation times of the grid positions, which makes it possible to reduce the duration of the irradiation. In addition, the equalization of the irradiation times of the grid positions can make sure that the irradiation of all grid positions takes long enough to ensure correct system functionality such as, for example, measurement of the beam position, and the time available for calculating the compensation values is also balanced, thus reducing the risk of the compensation value not being calculated and stored in time.

The measures under 4.a) through 4.c) are combinable with one another, and may each be combined with the measures described above under 1., 2., and 3.

In summary, the use of the grid-position-dependent real-time dose compensation according to the present invention makes it possible to reduce overdoses occurring during active beam adaptation (tracking), and to prevent underdosage. When combining the two methods, betters dose distributions may be expected than with interrupted irradiation (gating) or classical multiple irradiation (rescanning). However, in some cases it is even possible to dispense with the technically complex energy adaptation (longitudinal active beam compensation).

It will be readily apparent to those skilled in the art that the above-described embodiments are meant to be exemplary, and that the present invention is not limited thereto, but may be varied in many ways without departing from the scope thereof. It will also be clear that, regardless of whether the features are disclosed in the description, the claims, the figures or elsewhere, they also individually constitute essential elements of the present invention, even if they are described together with other features.

While the invention has been particularly shown and described with reference to preferred embodiments thereof, it will be understood by those skilled in the art that various changes in form and details may be made therein without departing from the spirit and scope of the invention.

What is claimed is:

1. A method for controlling the dose application during irradiation of a moving target volume in a body with an energy beam using a scanning method, the method comprising creating an irradiation plan including a plurality of grid positions (i, $1<=i<=N$) of the target volume for one or more irradiation cycles (j, $1<=j<=J$), wherein N and J are positive integers;

defining a grid-position-dependent nominal particle fluence in the irradiation plan for the irradiation of each of the grid positions;

capturing a motion of the body during the irradiation in order to determine a motion of the grid positions during the irradiation; and successively scanning the individual grid positions with the energy beam using a particle energy and a particle fluence that are controlled as a function of the grid position, so as to apply a grid-position-dependent dose at the corresponding grid position, the scanning including:

i1) prior to the irradiation of an i-th grid position of the plurality of grid positions, calculating a dose that was already received by the i-th position during the irradiation of previous grid positions (k, $1 \leq k < i$) during the irradiation cycle using the motion data;

i2) prior to the irradiation of the i-th grid position, calculating a compensation value ($\Delta D^i$) for the i-th grid position based on the dose that the i-th grid position is determined to have already received during the irradiation of the previous grid positions (k, $1 \leq k < i$);

i3) prior to the irradiation of the 1-th grid position, calculating a compensated particle fluence ($F^i_{comp}$) for the i-th grid position based on the compensation value ($\Delta D^i$) for the i-th grid position and a nominal particle fluence ($F^i_{nom}$) for the i-th grid position; and i4) irradiating the i-th grid position with the compensated particle fluence ($F^i_{comp}$) determined for the i-th grid position, steps i1) through i4) being carried out for the plurality of grid positions ($1 \leq i \leq N$).

2. The method as recited in claim 1,
wherein the calculating the compensation value ($D^i$) for the i-th grid position is carried out at least partly during the irradiation of the i-1-th grid position.

3. The method as recited in claim 1,
wherein during the irradiating, in order to calculate the compensation value ($\Delta D^i$) for the i-th grid position, dose changes received by the i-th grid position during the irradiation of all previously irradiated grid positions l are summed over all l from 1 to i−1, and the compensation value for the irradiation of the i-th grid position is calculated during the irradiation of the i-1-th grid position from the sum of the dose changes.

4. The method as recited in claim 1,
wherein the compensation value for the i-th grid position is a relative correction factor $$\frac{\Delta D^i}{D^{ii}_{ref}}$$

for the i-th grid position which is normalized with a reference dose ($D^{ii}_{ref}$) for the i-th grid position, and the correction factor is applied to the nominal particle fluence ($F^i_{nom}$) defined for the i-th grid position in the irradiation plan, so as to calculate the compensated particle fluence ($F^i_{comp}$) for the 1-th grid position.

5. The method as recited in claim 1,
wherein the applied particle fluence for all grid positions is controlled with a therapy control system that communicates with a control device for an accelerator and has a subsystem for controlling the particle fluence;

whereby the compensation value for the i-th grid position is stored in a memory of the subsystem thr controlling the particle fluence during the irradiation of the i-1-th grid position, and subsequently, the subsystem for controlling the particle fluence loads the compensation value for the i-th grid position from the memory and applies it to the nominal particle fluence defined for the i-th grid position in the irradiation plan, so as to subsequently irradiate the i-th grid position with the compensated particle fluence for the i-th grid position.

6. The method as recited claim 1,
wherein during the irradiation of the i-th grid position, dose changes are not calculated for all of the subsequent grid positions ($\geq i+1$) simultaneously, and wherein a dose change and compensation value are initially calculated for the i+1-th grid position, and the calculation of the dose changes and compensation values for the subsequent grid positions ($\geq i+2$) is performed later.

7. The method as recited in claim 1,
wherein during the irradiation of the i-th grid position, the dose changes are not calculated for all of the subsequent grid positions ($\geq i+1$) simultaneously, and wherein the dose changes are initially calculated only for the grid positions of the iso-energy layer in which the i-th grid position is located; and the dose changes for the grid positions of the subsequent iso-energy layers are calculated at least partly during a beam pause between the irradiation of the iso-energy layers.

8. The method as recited in claim 1,
wherein if prior to the irradiation the i-th grid position, a dose change of the i-th grid position is already greater than or equal to the reference dose defined for the i-th grid position in the irradiation plan, then the i-th grid position is skipped or irradiated with a minimum dose determined prior to the irradiation.

9. The method as recited in claim 1,
wherein during the irradiation, the intensity of the beam is adjusted to the particle fluence to be applied to the respective grid positions.

10. The method as recited in claim 1,
wherein a grid-position-dependent distribution of the particle fluences for the grid positions following an irradiation pause are calculated for several motion phases (m) and evaluated using a quality index (Q), and the irradiation of the next iso-energy layer is started after a beam pause between the irradiation of two iso-energy layers based on the quality index (Q).

11. The method as recited in claim 10,
wherein at least one of the following evaluation criteria is included in the quality index (Q):
i) a similarity of compensated particle fluences of the grid positions;
ii) deviations of the compensated particle fluences from the particle fluences of the reference doses;
iii) reduction of overdoses to the subsequent grid positions;
iv) a time until the associated motion phase is expected to be reached.

12. The method as recited in claim 1,
wherein the irradiation includes active adaptation of the beam in at least one dimension (x,y,z) as a function of the determined motion data of the grid positions of the target volume so as to compensate for the motion of the currently irradiated grid position of the target volume in the at least one dimension.

13. The method as recited in claim 1,
wherein the motion of the grid positions in the longitudinal direction (z) are determined to allow calculation of the grid-position-dependent compensation value, but the irradiation does not include active adaptation of the beam energy ($E^i$) as a function of the determined motion data of the grid positions of the target volume.

14. The method as recited in claim 1
wherein the irradiation includes active adaptation of at least one lateral beam position (x, y) as a function of the determined motion data of the grid positions of the target volume (32) in order to compensate for the motion of the currently irradiated grid position of the target volume in the at least one lateral dimension (x, y); and the motions of the grid positions in the longitudinal direction (z) are captured to allow the grid-position-dependent compensation value to be calculated despite the motion, but the irradiation does not include active adaptation of the beam energy as a function of the determined motion data of the grid positions of the target volume.

15. The method as recited in claim 1,
wherein the irradiation is divided into a plurality of irradiation cycles (j, $1 \leq j \leq J$), each with a fraction of the reference doses, and dose changes received by the i-th grid position in the previous irradiation cycles (<j) and dose changes received by the i-th grid position during the irradiation of the previous grid positions in the current irradiation cycle (j) are taken into account in a calculation of the compensation factor for the i-th grid position in an irradiation cycle (j).

\* \* \* \* \*